(12) United States Patent
Hill et al.

(10) Patent No.: US 7,431,900 B2
(45) Date of Patent: Oct. 7, 2008

(54) HYDROGEN PEROXIDE VAPOR SYSTEM WITH REPLACEABLE DESICCANT CARTRIDGE

(75) Inventors: Aaron L. Hill, Erie, PA (US); Arthur T. Nagare, Erie, PA (US); Frank E. Dougherty, Fairview, PA (US); Stanley M. Voyten, Albion, PA (US)

(73) Assignee: Steris Inc, Temecula, CA (US)

( * ) Notice: Subject to any disclaimer, the term of this patent is extended or adjusted under 35 U.S.C. 154(b) by 1037 days.

(21) Appl. No.: 10/377,557

(22) Filed: Feb. 28, 2003

(65) Prior Publication Data

US 2003/0164091 A1 Sep. 4, 2003

Related U.S. Application Data

(60) Provisional application No. 60/361,129, filed on Feb. 28, 2002.

(51) Int. Cl.
*A61L 9/00* (2006.01)
*A61L 2/00* (2006.01)
*B01D 24/00* (2006.01)
*B01D 53/02* (2006.01)
*F26B 5/06* (2006.01)

(52) U.S. Cl. ............................ 422/305; 422/1; 422/5; 422/28; 422/32; 422/34; 422/29; 422/30; 422/244; 422/292; 422/295; 422/298; 422/299; 422/300; 422/302; 422/307; 55/522; 95/90; 95/91; 95/16; 95/118; 95/141; 95/148; 95/230; 95/231; 95/237; 95/274; 95/900; 95/902; 95/903; 96/106; 96/108; 96/118; 96/134; 96/143; 96/147; 96/223; 96/226; 96/227; 96/295; 34/294; 34/299; 34/300

(58) Field of Classification Search .................. 422/1, 422/5, 28–30, 32, 34, 244, 292, 295, 297–300, 422/302, 305, 307; 55/522, DIG. 17; 95/91, 95/141, 116–118, 230–231, 237, 274, 900, 95/902–903; 96/108, 118, 134, 143, 147, 96/223, 226–227, 295; 34/294, 299, 300; 261/DIG. 34
See application file for complete search history.

(56) References Cited

U.S. PATENT DOCUMENTS

| | | | | |
|---|---|---|---|---|
| 2,572,311 | A | * | 10/1951 | Burd ............................ 137/204 |
| 3,552,034 | A | * | 1/1971 | May, Jr. .......................... 34/80 |
| 3,705,480 | A | * | 12/1972 | Wireman .................... 96/117.5 |
| 4,131,442 | A | * | 12/1978 | Frantz ........................... 96/137 |

(Continued)

FOREIGN PATENT DOCUMENTS

| | | | |
|---|---|---|---|
| EP | 0 608 606 A1 | | 8/1994 |
| EP | 0 774 263 A1 | | 5/1997 |
| GB | EP 0 774 263 A1 | * | 5/1997 |

*Primary Examiner*—Jill Warden
*Assistant Examiner*—Monzer R Chorbaji
(74) *Attorney, Agent, or Firm*—Fay Sharpe LLP

(57) ABSTRACT

A hydrogen peroxide vapor generation unit (10) receives hydrogen peroxide and water solution at an interface (20) and interconnects with an air dryer (14) by way of nipples (72, 92). In one embodiment, the dryer includes a clamping assembly (42) which is latched (74, 94) with the nipples and which receives a disposable desiccant cartridge (40). In an alternate embodiment, a reusable desiccant cartridge (40') is connected directly to the nipples (72, 92). When the desiccant cartridge (40') is saturated, it is removed and placed in a regenerator unit (120). A regenerated cartridge is installed in its place.

24 Claims, 7 Drawing Sheets

U.S. PATENT DOCUMENTS

| | | | | |
|---|---|---|---|---|
| 4,594,082 A | * | 6/1986 | Catherwood, Sr. | 96/138 |
| 4,745,772 A | * | 5/1988 | Ferris | 62/292 |
| 4,848,989 A | * | 7/1989 | Maeda | 55/319 |
| 4,909,999 A | * | 3/1990 | Cummings et al. | 422/298 |
| 4,966,697 A | * | 10/1990 | Rosaen | 210/232 |
| 5,114,003 A | * | 5/1992 | Jackisch et al. | 206/204 |
| 5,173,258 A | * | 12/1992 | Childers | 422/27 |
| 5,482,541 A | * | 1/1996 | Maier-Laxhuber et al. | 96/117.5 |
| 6,077,480 A | * | 6/2000 | Edwards et al. | 422/28 |
| 6,488,902 B1 | * | 12/2002 | DeCato et al. | 423/210 |

* cited by examiner

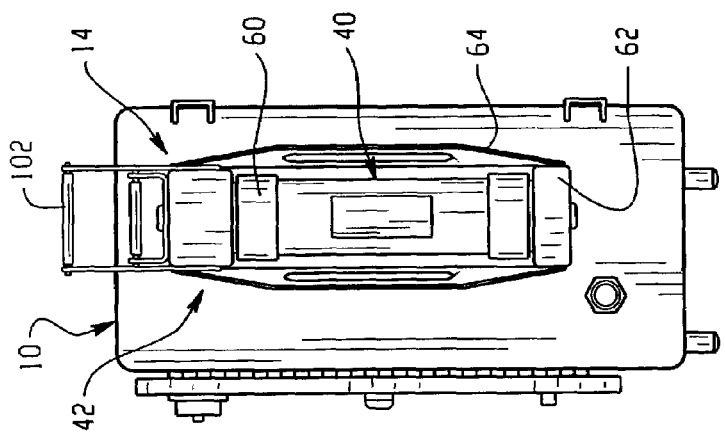
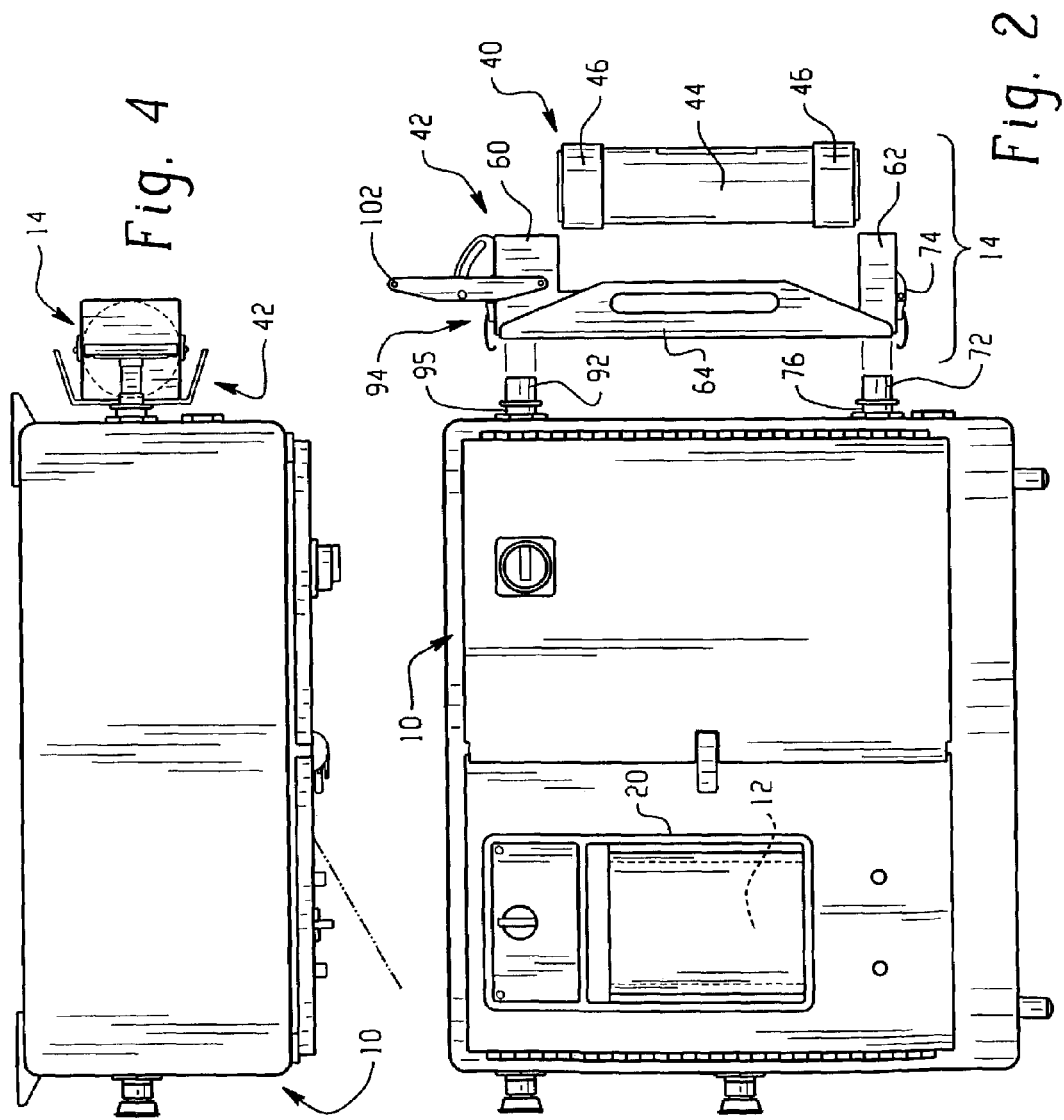

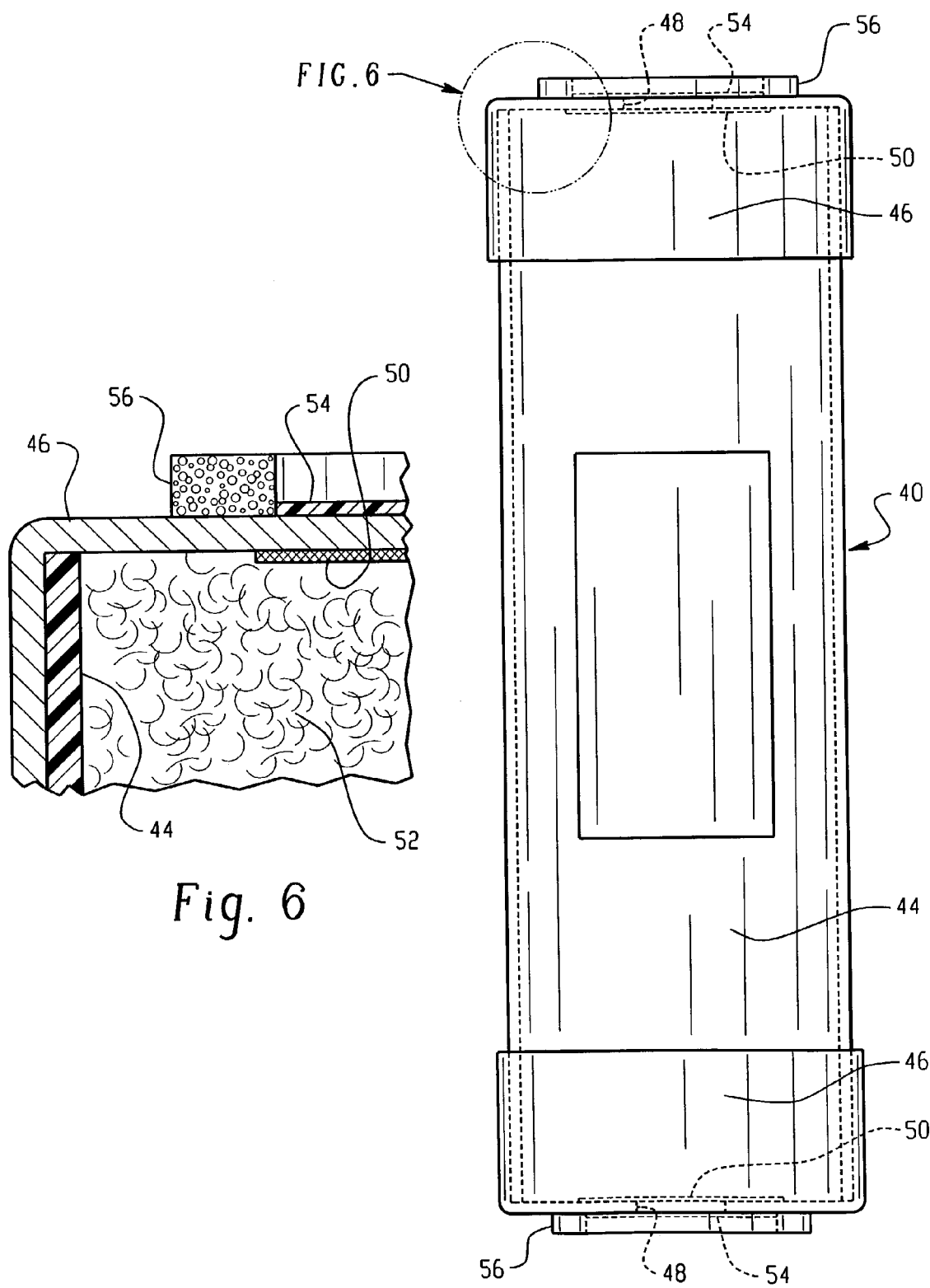

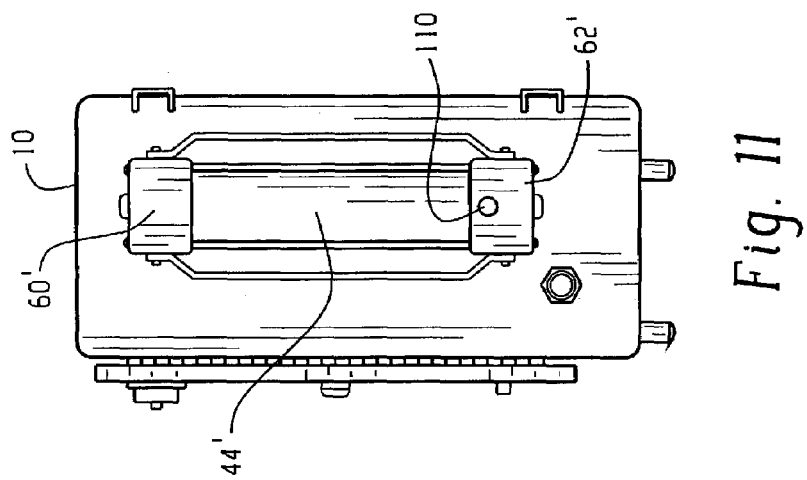
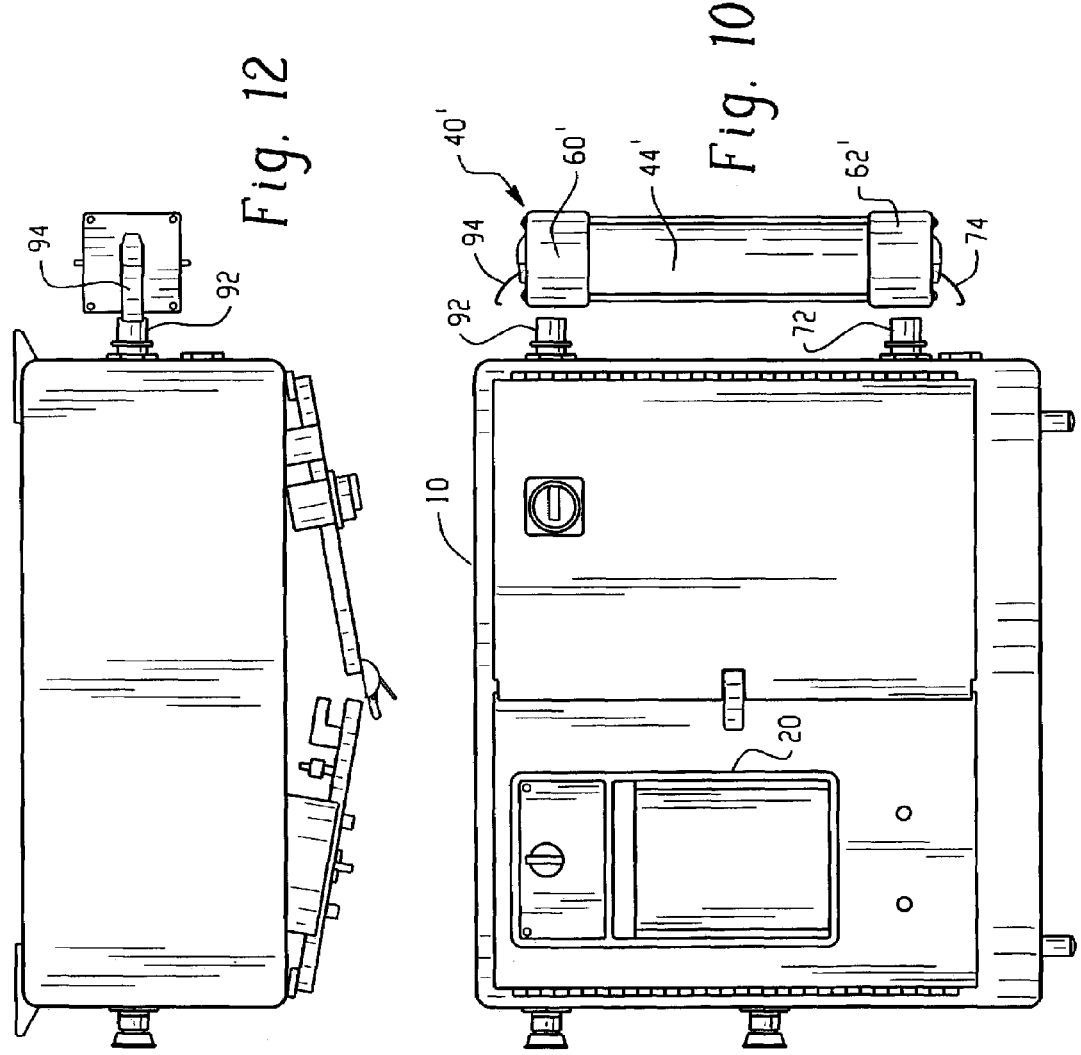

HYDROGEN PEROXIDE VAPOR SYSTEM WITH REPLACEABLE DESICCANT CARTRIDGE

This application claims the benefit of U.S. Provisional application Serial No. 60/361,129, filed Feb. 28, 2002.

BACKGROUND OF THE INVENTION

The present invention relates to the peroxy vapor treatment arts, more particularly to hydrogen peroxide vapor sterilization and disinfection. The invention finds particular application in conjunction with hydrogen peroxide vapor sterilization systems in which peroxide vapor is entrained in dry air which has been dried with a desiccant and will be described with particular reference thereto. It is to be appreciated that the present invention may be used with other peroxy vapors in conjunction with disinfection, sanitation, and other treatment processes.

Heretofore, a solution of hydrogen peroxide and water have been vaporized and entrained in dry air. The vapor and air are pumped into a sterilization or other treatment chamber. The hydrogen peroxide reacts with microbial and other decontaminants in an oxidizing reaction which deactivates them and converts the vapor molecule from peroxide to water. To maintain a preselected concentration of hydrogen peroxide in the chamber, air and vapor from the chamber are recirculated to the vaporizer. Hydrogen peroxide vapor in the withdrawn air is decomposed catalytically or by heat to water vapor. The water vapor is then removed from the air, leaving dry air to be recirculated to the vaporizer.

One technique for drying the air was by condensation. However, condensation requires relatively expensive compressors and refrigeration units. Moreover, such condensation units typically fail to dry the air to a consistent level of humidity.

Consistent and lower level of humidity have been achieved by passing the air and water vapor through a desiccant. Although desiccants dry the air consistently to a low humidity, it typically takes longer to regenerate a desiccant than to saturate it. One way to meet these demands was through the use of a desiccant wheel. The air and water vapor were passed through a first portion or section of a desiccant wheel until that section became substantially saturated. The wheel was then indexed, bringing a new desiccant portion or section into the air and water vapor flow path. The saturated portion of the desiccant was subject to a regeneration process over the next several indexed positions of the wheel. Such onboard systems for regenerating desiccant were not only expensive and mechanically complex, but also added significant weight and bulk to portable hydrogen peroxide generation systems.

The present invention provides a new and improved desiccant drying system which overcomes the above-referenced problems.

SUMMARY OF THE INVENTION

In accordance with one aspect of the present invention, a peroxy vapor system includes a liquid peroxy solution interface for receiving a source of liquid peroxy solution. A vaporizer vaporizes the liquid peroxy solution and entrains it in air. A replaceable desiccant dryer is connected with the vaporizer for drying the air.

In accordance with another aspect of the present invention, a replaceable desiccant cartridge is provided for a vapor hydrogen peroxide generating system that includes a liquid peroxy solution cartridge interface for interconnection with cartridges of liquid peroxy solution, a vaporizer for vaporizing the liquid solution and entraining the vapor in air, a clamping unit which receives the desiccant cartridge to supply the dry air to the vaporizer, the clamping unit including a pair of end elements between which the desiccant cartridge is received, a piston mounted in one of the end elements which piston has a sealing face, a second sealing face on the other end element with the sealing faces facing each other to receive the desiccant cartridge therebetween, and a mechanism for retracting the piston to facilitate removal of a saturated desiccant cartridge and receipt of an unsaturated desiccant cartridge. The disposable desiccant cartridge includes a tubular chamber with enclosures at either end and a desiccant material received in the tubular chamber. An inlet aperture is defined in one end closure and an outlet aperture is defined in the opposite end closure. Annular gaskets surround the apertures of the end closures. A screen element at each end aperture retains the desiccant material within the tubular element. Removable seals close the end apertures to prevent humidity from entering the desiccant cartridge before the seals are removed.

In accordance with another aspect of the present invention, a dryer is provided for a vapor peroxy generation system which includes a vaporizer for vaporizing a peroxy composition and water solution and entraining the vapor in dry air, a peroxy vapor discharge outlet through which the peroxy vapor and air are discharged, a vapor and air recovery inlet into which partially spent peroxy vapor, water vapor, and air are returned, a dry air inlet nipple projecting from the peroxy vapor unit for supplying the dry air to the vaporizer, which inlet nipple has a latch engaging surface, and a recovered air and vapor discharge nipple also having a latching surface. The dryer includes a first end element having a bore for receiving the dry air inlet nipple in a fluid tight relationship and a second end element having a bore for receiving the recovered air and vapor discharge nipple in a fluid tight relationship. A desiccant chamber is connected between the first and second end elements. A first latch mechanism mounted to the first end element engages the dry air inlet nipple latching surface for latching the first end element to the dry air inlet nipple. A second latch mounted to the second end element engages the recovered air and vapor discharge nipple latch surface for latching the second end element to the recovered vapor and air discharge nipple.

In accordance with another aspect of the present invention, a quick connect/disconnect apparatus is provided. A holder has a first portion and a second portion. The first and second portions are rigidly connected and spaced apart so as to receive a cartridge therebetween. The first portion has an inlet port and an outlet port. The second portion also has an inlet port and an outlet port. The outlet port of the first section is fluidicly connectable to a first port of the cartridge and the inlet port of the second portion is fluidicly connectable to the second port of the container. The first portion of the holder has a clamping mechanism operable after the cartridge has been placed in the holder to clamp the cartridge between the first and second portions such that the output port of the first portion is in alignment with the first port of the container and the input port of the second portion is in alignment with the second port of the container. At least one clamp is located on the holder engageable with a fixture located on a device to securely affix the holder to the device.

In accordance with another aspect of the present invention, a quick connect/disconnect desiccant dryer is provided. An upper portion and a lower portion are spaced apart and a container is rigidly affixed to the apparatus that extends between the upper portion and the lower portion. The container holds a desiccant. The upper portion and the lower portion each have an input port and an output port. The output port of the upper portion is fluidically connected to a first port of the container; and the input port of the lower portion is fluidically connected to the second port of the container. At least one clamp which is located on the apparatus is engageable with a fixture located on a device to securely affix the dryer to the device.

One advantage of the present invention resides in its simplicity and low cost.

Another advantage of the present invention resides in the assurance of adequate desiccant drying capacity.

Another advantage of the present invention resides in the assurance of dry air with a predictable low humidity level.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

FIG. 2 is a side-view of the peroxy vapor generation system;

FIG. 3 is an end-view of the system of FIG. 2;

FIG. 4 is a top view of the vaporizer unit and disposable dryer cartridge embodiment of FIGS. 2 and 3;

FIG. 5 is an enlarged view of the desiccant cartridge of FIGS. 2-4;

FIG. 6 is an enlarged sectional view of an end portion of the cartridge of FIG. 5;

FIG. 10 is an side view of the vaporizer system of FIG. 2 with an alternate, reusable dryer;

FIG. 11 is an end view of the alternate embodiment of FIG. 10;

FIG. 12 is a top view of the vaporizer unit and reusable dryer cartridge embodiment of FIGS. 10 and 11 with front access panel doors partially open;

DETAILED DESCRIPTION OF THE PREFERRED EMBODIMENTS

Figure 1:
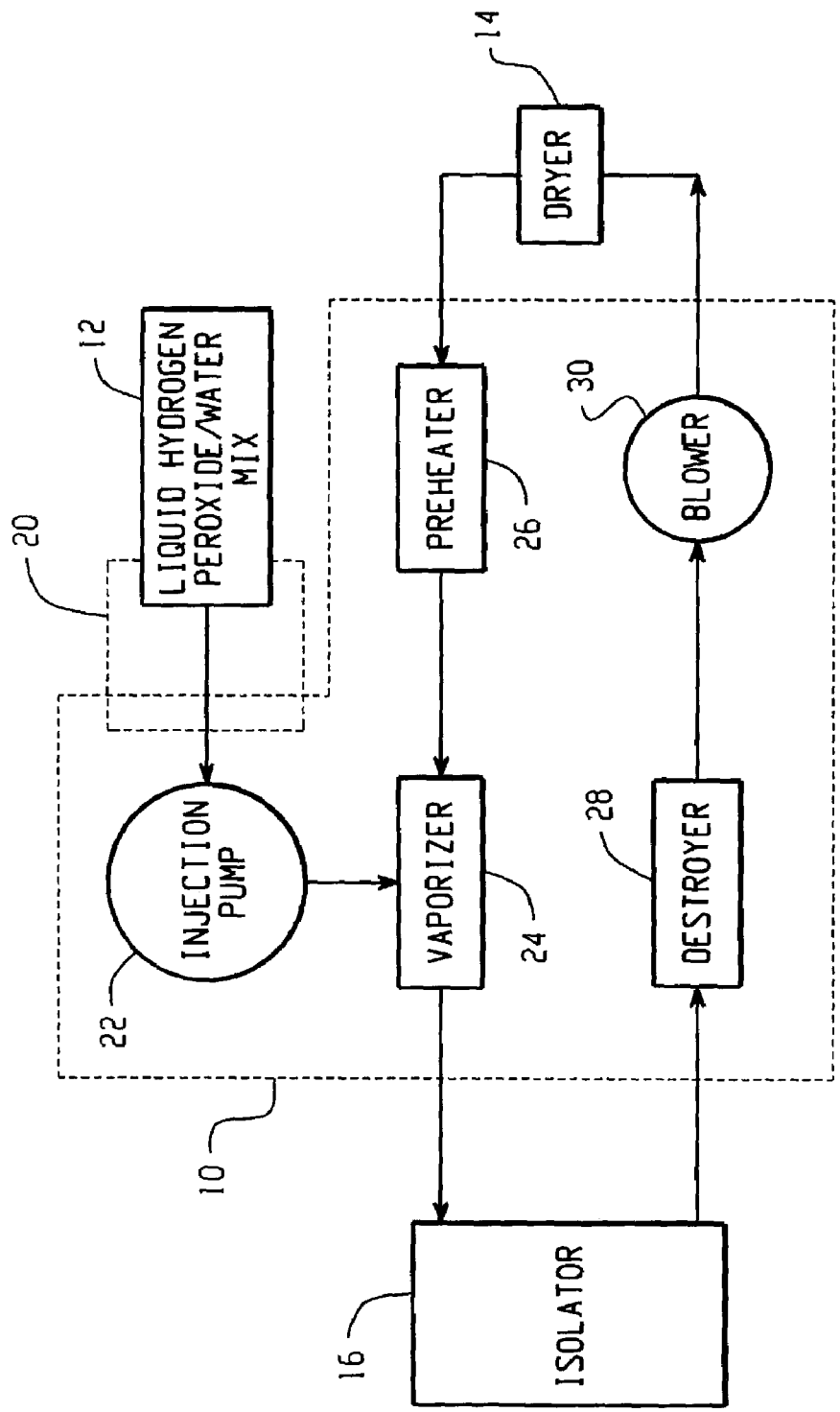
FIG. 1 is a diagrammatic illustration of a hydrogen peroxide vapor decontamination system in accordance with the present invention.

With reference to FIGS. 1, 2, 3, and 4, a vapor generation unit 10 vaporizes a peroxy solution from a solution source 12 and entrains the vapor in dry air which has been dried by a dryer 14. The dry air and vapor are conveyed to a treatment chamber, such as an isolator 16.

In the preferred embodiment, the peroxy solution source is a container or cartridge of hydrogen peroxide in water solution which is received in a cartridge interface 20. Once in the cartridge interface, the cartridge is interconnected with a dip tube assembly for withdrawing the solution. Although a solution of hydrogen peroxide in water vapor is preferred, other solutions are contemplated, such as peracetic acid and water, other peroxy compounds and water, peroxy compounds in alcohol and water, and the like. In a preferred embodiment, the hydrogen peroxide and water solution is 35-50% hydrogen peroxide.

The vaporizer system includes an injection pump 22 which injects metered amounts of the peroxy solution into a vaporizer 24. The vaporizer, in a preferred embodiment, is a heated surface, such as a heated plate or the interior surface of a bore onto which the peroxy solution is sprayed or injected forming peroxy and water vapor. Dry air from the dryer 14 is preheated in a preheater 26 and supplied to the vaporizer to entrain the hydrogen peroxide or other peroxy vapor and water vapor. The vapor entrained in the air is supplied to the treatment chamber 16.

In the treatment chamber, hydrogen peroxide vapor interacts with microbes and other contaminants in an oxidation reaction, deactivating the microbial material and leaving water vapor suspended in the air. Thus, with time, the concentration of hydrogen peroxide in the treatment chamber drops. To maintain the concentration of hydrogen peroxide vapor, a portion of the vapor and air is withdrawn and fed through a destroyer 28, such as copper pellets. The copper pellets catalytically degrade the remaining peroxide vapor into water vapor and oxygen. A blower 30, which provides the motive force to move the air and vapor, pumps the air and water vapor to the dryer 14. Desiccant in the dryer absorbs the water vapor such that air of accurately predictable low humidity is discharged to the preheater 26. In this manner, air of known humidity is supplied to the vaporizer, permitting the vaporizer to optimize the concentration of peroxide vapor without condensation. It will be noted that if a significant amount of unexpected water vapor were returned to the vaporizer, the additional vapor content of the saturated air could push the total vapor content of one or both of the peroxide and the water vapor beyond the condensation point.

In a preferred embodiment, the dryer 14 includes a disposable desiccant cartridge 40 which is clamped into a clamping assembly 42.

With reference to FIGS. 5 and 6, the desiccant cartridge includes a cylindrical tube 44 which is closed at either end with end caps 46 to form a cartridge of preselected length. Apertures 48 are defined centrally in each end cap to allow for the passage of gas into and out of the cartridge. The apertures are covered on the inside by disks 50 of screening material to retain a desiccant 52. A water vapor impermeable end seal 54 is adhesively adhered over an exterior of each opening to prevent the desiccant within the cartridge from absorbing water vapor before it is mounted in the clamping assembly 42. The aperture in each end is surrounded by a resilient gasket 56, such as a closed cell foam of a material which is inert to hydrogen peroxide or other circulated gases.

Figure 7:
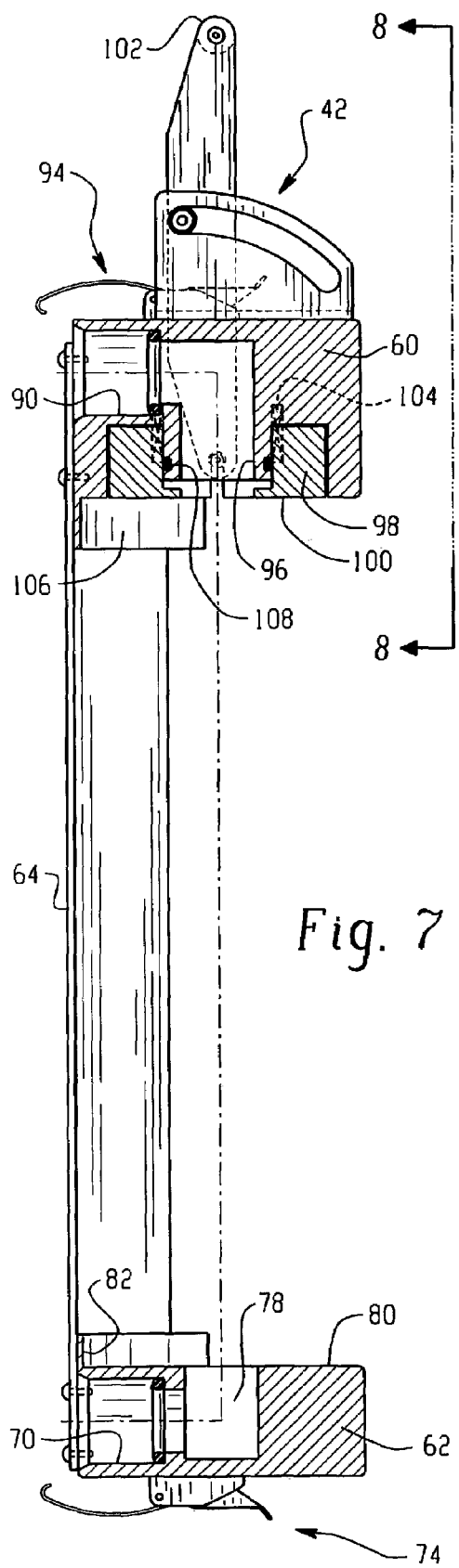
FIG. 7 is a side-sectional view of the desiccant cartridge receiving assembly of FIGS. 2-4.
Figure 8:
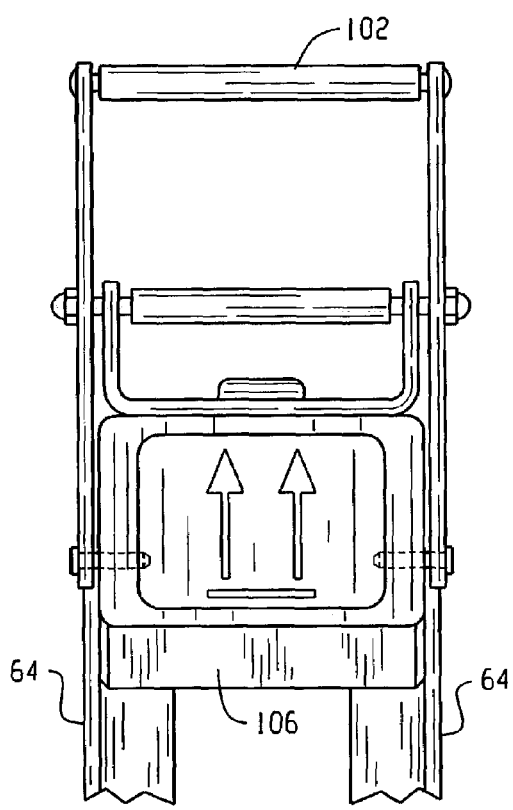
FIG. 8 is a front view of an upper portion of the assembly of FIG. 7.
Figure 9:
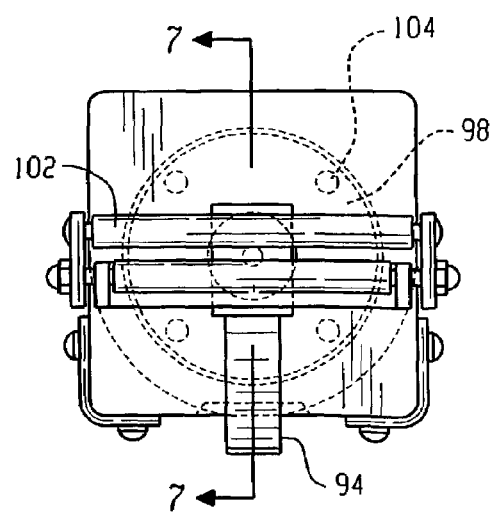
FIG. 9 is a top view of the assembly of FIG. 7.
Figure 13:
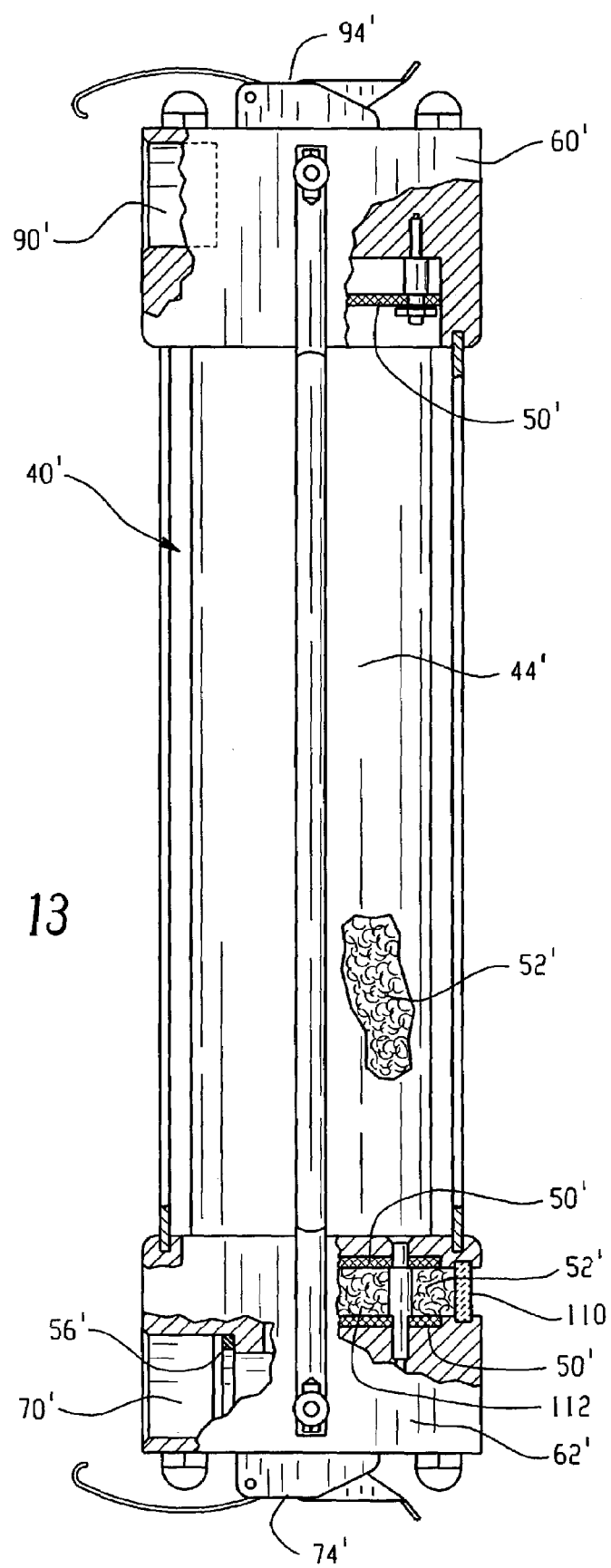
FIG. 13 is a side sectional view of the reusable dryer cartridge of FIGS. 10-12.

With reference again to FIGS. 2 and 3, and further reference to FIGS. 7, 8, and 9, the clamping assembly 42 includes a pair of end elements 60, 62 and pair of tie angles 64 which maintain the end pieces 60, 62 in a preselected, fixed spaced relationship. The lower end element 62 includes an inlet connection port or bore 70 for interconnection with an outlet nipple 72 of the vapor generator assembly 10. A latch assembly 74 engages a lip 76 around the outlet nipple to maintain the clamping assembly 42 attached to the vapor generator. The inlet port includes an L-shaped passage terminating in an outlet port 78 adjacent an inlet to the cartridge. The lower assembly has a smooth sealing face 80 surrounding the outlet port 78 to provide an air-tight seal with the lower gasket 56.

The lower assembly includes an upstanding, semi-circular guide portion 82 which receives and positions a lower end of the cartridge centered on the outlet port 78.

The upper element 60 includes an outlet port 90 which is dimensioned to be received in a fluid-tight relationship with a nipple 92 of an inlet port for dry gas on the vaporizer unit 10. A latch assembly 94 locks the upper element to the nipple assembly lip 95. The upper element 60 includes an L-shaped passage terminating in an inlet port 96. The inlet port 96 is surrounded by a piston 98 of larger diameter than the gasket 56 of the desiccant cartridge. The piston defines a smooth, polished sealing face 100 which forms a sealing relationship with the desiccant cartridge gasket. The piston 98 is retracted by pulling a handle 102 toward the user, away from the vaporizing unit 10. Springs 104 bias the piston toward engagement with the gasket of the desiccant cartridge. When a desiccant cartridge is to be inserted, the handle 102 is pushed away from the user, retracting the piston. This loosens the seal between the piston and the gasket of the used desiccant cartridge which is removed. The adhesive seals 54 of the new desiccant cartridge are removed and the desiccant cartridge is inserted into the latching unit 40 until its rear surfaces engage the alignment surface 84 of the lower element 62 and a matching alignment surface 106 of the upper element 60. The handle 102 is returned to the angled position allowing the springs 104 to bias the sealing face 100 of the piston 98 into a fluid-tight seal with the upper gasket of the desiccant cartridge. An O-ring 108 between the piston 98 and the upper element 60 prevents vapor from passing between the piston and the upper end element.

In one preferred embodiment, the desiccant cartridge is sized in accordance with the anticipated hydrogen peroxide consumption. In one embodiment, the dryer is sized to accommodate the moisture from one cycle of the largest enclosure under worst case conditions. In this embodiment, the desiccant cartridge is replaced at the beginning of each cycle. In another embodiment, the desiccant cartridge is sized to absorb all of the water vapor that is generated by the contents of the hydrogen peroxide cartridge. In this embodiment, the desiccant cartridge is replaced each time the hydrogen peroxide cartridge is replaced. In another embodiment, the desiccant cartridge is sized to be able to hold the water generated by a plurality of the hydrogen peroxide cartridges. As yet another alternative, the desiccant cartridge includes an indicator which provides a visual indication that the cartridge is nearing saturation and should be replaced. As yet another alternative, the vaporization unit 10 includes a moisture sensor which senses the humidity of the air entering the preheater. When the humidity starts to rise, the vaporization unit provides a visual or audio signal indicating that the desiccant cartridge 40 is due for replacement.

As another alternative, the alignment surfaces 82, 106 have projections that are received in corresponding recess in the cartridge 40 to ensure accurate alignment. In another alternative, mating surface 80 of the lower element 62 and the lower end cap have mating projections and recesses outside of the perimeter of the gasket 56 to assure alignment. When the handle 102 is pushed to retract the piston, a pawl holds the piston 98 retracted. A projection or element on the upper end cap interacts with the pawl directly or through a connecting linkage to release the piston only when the top of the cartridge is properly received to release the piston. As another option, cutters can be provided on the lower element 62 and the piston 98 to open the end seals 54 when the cartridge is properly aligned.

With reference to FIGS. 10-13, in another embodiment, a dryer cartridge 40' is attached directly to the nipples 72, 92 of the vaporizer unit 10. This embodiment includes a first or top element 60' and a second or lower end element 62' which are interconnected by a desiccant cylinder 44'. The upper end element includes a bore 90' with a gasket configured to receive the uppermost nipple 92 in a fluid-tight relationship; and the lower end element defines a lower well 70' and a gasket 56' configured to receive the lower nipple 72 in a fluid tight seal. A lower latch 74' engages the latching surface of the lower nipple 72 and an upper latch 94' engages the latch surface of the upper nipple 92. Screen elements 50' are disposed adjacent upper and lower outlets of the cartridge to contain a desiccant 52' therebetween. A glass sight 110 enables the operator to view a lower desiccant chamber 112 that is defined between a pair of the lower screens 50'. The color of the desiccant is an indication to the user whether or not a dryer has been regenerated. In the preferred embodiment, the desicacant turns clear soon after the dryer is put in use. The desiccant turns color (blue in this case) after regeneration.

Preferably, all components of the reusable desiccant cartridge are constructed of metal or other materials capable of withstanding repeated exposure to temperatures on the order of 150° C. Alternately, the cartridge can be a single use cartridge that is disposed after being used.

Figure 14:
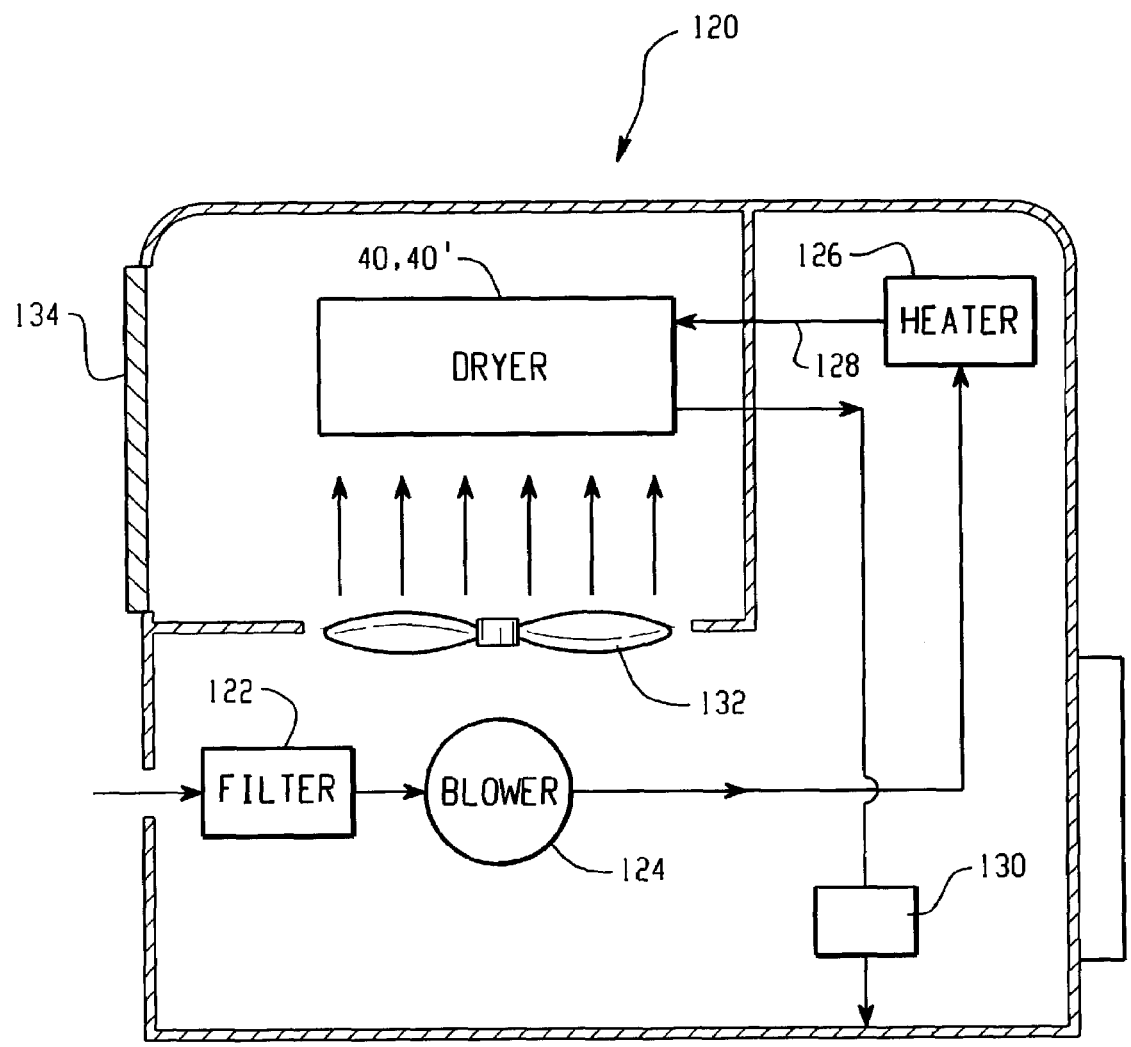
FIG. 14 is a diagrammatic illustration of a regenerator unit for the cartridge of FIGS. 10-13.

When the desiccant cartridge is saturated or cannot hold the moisture generated by the next cycle to be run, the latches 74', 94' are released and the drying cartridge is removed and replaced with a regenerated cartridge. With reference to FIG. 14, the saturated cartridge is placed in a regeneration unit 120. The regeneration unit includes nipples of the same size and spacing as nipples 72, 92 in the second embodiment which are plug into the passages 70', 90'. For cartridges of the embodiment of FIG. 5, the manifold 128 includes mating top and bottom connections. The regeneration unit includes a filter, preferably a HEPA filter 122 which removes airborne contaminants. A blower 124 blows the filtered air through a heater 126 to a manifold 128. The manifold is connected with one or more desiccant cartridges 40' which are to be regenerated. The heated air, heated to about 150° C., is blown through the desiccant entraining the absorbed water, and discharged to the atmosphere. After the desiccant is fully regenerated, as determined by measuring the temperature of the discharged air with a temperature switch 130, based on time, or other factors, the circulation of heated air through the desiccant is stopped and a cooling fan 132 is started. The cooling fan cools the desiccant cartridge back to room temperature while the ports of the cartridge remain closed. A lockable door 134 is released once the desiccant cartridges have cooled to a temperature that is safe to handle. The desiccant cartridges remain connected to the manifold to prevent the cooling air from entering the chambers where humidity from the cooling air would be absorbed.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A peroxy vapor system including:
   a liquid peroxy solution interface for receiving a source of liquid peroxy solution; a clamping unit which receives and clamps a desiccant cartridge through which air is drawn to dry the air a vaporizer for vaporizing the liquid peroxy solution and entraining the vapor in air; and, a replaceable desiccant dryer removably connected with the vaporizer for drying the air in which the vapor is being entrained, the desiccant dryer including:
a tubular chamber with end closures at either end;
a desiccant material which absorbs water vapor in the tubular chamber;
an inlet a aperture defined in one end closure and an outlet aperture defined in an opposite end closure;
annular gaskets surrounding the apertures of the end closures; a piston mounted in one of the end elements, the piston having a sealing face for engaging one end of a desiccant cartridge in a sealing relationship therewith; a means for retracting the piston to facilitate removal of a saturated desiccant cartridge and receipt of an unsaturated desiccant cartridge
a screen element at each end aperture for retaining the desiccant material within the tubular chamber; and
removable, peel-off, and water vapor impermeable seals closing the end apertures to prevent ambient humidity from being absorbed by the desiccant material before the seals are removed.

2. The system as set forth in claim 1 further including:
a window disposed in one of the end closures.

3. A peroxy vapor system including:
a liquid peroxy solution interface for receiving a source of liquid peroxy solution;
a vaporizer for vaporizing the liquid peroxy solution and entraining the vapor in air;
a replaceable desiccant dryer cartridge removably connected upstream of the vaporizer for drying the air in which the vapor is to be entrained; and,
a clamping element which receives and clamps the desiccant cartridge such that the air flowing to the vaporizer passes therethrough and is dried, the clamping element including:
a pair of end elements;
a piston mounted in one of the end elements, the piston having a sealing face for engaging a cartridge gasket in a sealing relationship therewith;
a second gasket sealing face on the other end element;
a mechanism for retracting the piston to facilitate removal of a saturated desiccant cartridge and receipt of an unsaturated desiccant cartridge.

4. The system as set forth in claim 3 wherein the clamping unit further includes:
springs for biasing the piston into contact with the desiccant cartridge; and,
wherein the retracting mechanism includes a manually operable lever which is operated to move the piston against the springs retracting it.

5. The system as set forth in claim 3 further including:

an alignment bracket associated with each end element for aligning the desiccant cartridge gaskets with the gasket sealing faces of the clamping unit.

6. The system as set forth in claim 3 wherein the vaporizer unit includes a pair of projecting nipples, each having a latch engaging surface; and wherein the end elements each include:

a bore for receiving one of the nipples in a fluid-tight arrangement, and a latch arrangement for engaging the nipple latch engaging surface for latching the end elements to the nipples.

7. A peroxy vapor system including:

a liquid peroxy solution interface for receiving a source of liquid peroxy solution;

a vaporizer for vaporizing the liquid peroxy solution and entraining the vapor in air;

a replaceable desiccant dryer removably connected with the vaporizer for drying the air in which the vapor is being entrained, the desiccant dryer including:

a desiccant chamber connected between a pair of end elements, one of the end elements defining an inlet bore for air to be dried and the other end element defining an outlet bore for dry air;

a pair of rigidly mounted nipples for interconnecting the vaporizer with the desiccant dryer, the bores of each of the end elements receiving one of the nipples in a fluid tight relationship and in mechanical relationship such that the desiccant dryer is supported on the nipples; and a latch for latching the end elements to the nipples.

8. The system as set forth in claim 7 wherein the desiccant chamber is detachable from the end elements, the end elements including:

a piston mounted in one of the end elements, the piston having a sealing face for engaging one face of the desiccant chamber in a sealing relationship therewith;

a second sealing face on the other end element;

a mechanism for retracting the piston to facilitate removal of a saturated desiccant chamber and receipt of a replacement desiccant chamber.

9. The system as set forth in claim 7, further including:

a regeneration oven for regenerating saturated desiccant dryers, the regeneration oven including a pair of nipples configured to be received in the bores of the desiccant dryer end elements.

10. A replaceable desiccant cartridge for a vapor hydrogen peroxide generating system that includes a liquid peroxy solution cartridge interface for interconnection with cartridges of liquid peroxy solution, a vaporizer for vaporizing the liquid solution and entraining the vapor in dry air, a unit which receives the desiccant cartridge to supply the dry air to the vaporizer, a pair of elements one of which includes a dry air passage for discharging dry air from the desiccant cartridge and the other includes a humid air supply passage for receiving humid air, the desiccant cartridge being received between the pair of end elements in a fluid tight relationship, a piston mounted in one of the end elements, the piston having a first sealing face, a second sealing face on the other end element, the sealing faces facing each other to receive the desiccant cartridge therebetween, and a mechanism for retracting the piston to facilitate removal of a saturated desiccant cartridge and receipt of an unsaturated desiccant cartridge, the disposable desiccant cartridge comprising:

a tubular chamber with end closures at either end;

a desiccant material received in the tubular chamber;

an inlet aperture defined in one end closure and an outlet aperture defined in an opposite end closure;

annular gaskets surrounding the apertures of the end closures;

a screen element at each end aperture for retaining the desiccant material within the tubular element; and removable seals closing the end apertures to prevent humidity from entering the desiccant cartridge before the seals are removed.

11. A dryer for a vapor peroxy generation system including:

a vaporizer which vaporizes a peroxy composition and water solution and entrains the vapor in dry air;

a peroxy vapor discharge outlet through which the peroxy vapor and air are discharged;

a vapor and air recovery inlet into which partially spent peroxy vapor, water vapor, and air are returned;

a dry air inlet nipple projecting from the vapor peroxy generation system for supplying the dry air to the vaporizer, the inlet nipple having a latch engaging surface;

a recovered air and vapor discharge nipple through which the partially spent peroxy vapor water vapor and air are discharged, the discharge nipples having a latching surface;

the dryer removably mounted between the dry air inlet nipple and the recovered air and vapor discharge nipple and comprising:

a first end element having a bore for receiving the dry air inlet nipple in a fluid tight relationship, a second end element having a bore for receiving the recovered air and vapor discharge nipple in a fluid tight relationship, a desiccant chamber connected between the first and second end elements, a first latch mounted to the first end element for engaging the dry air inlet nipple latching surface for latching the first end element to the dry air inlet nipple, a second latch mounted to the second end element for engaging the received air and vapor discharge nipple latch surface for latching the second end element to the recovered air and vapor discharge nipple; a piston mounted in one of the end elements, the piston having a sealing face for engaging one end of a desiccant cartridge in a sealing relationship therewith; a means for retracting the piston to facilitate removal of a saturated desiccant cartridge and receipt of an unsaturated desiccant cartridge.

12. The dryer as set forth in claim 11 further including:
springs for biasing the piston assembly into contact with the desiccant cartridge; and,
wherein the retracting means includes a manually operable lever which is operated to move the piston against the springs retracting it.

13. The dryer as set forth in claim 11 further including:
an alignment bracket associated with each end piece for aligning the desiccant cartridge with the sealing surfaces of the end elements.

14. The dryer as set forth in claim 11 further including:
a desiccant cartridge regeneration system which receives the end elements and interconnected desiccant chamber and regenerates the desiccant therein.

15. A quick connect/disconnect desiccant dryer comprising:
(a) an upper portion and a lower portion that are spaced apart and a container extending between the upper portion and the lower portion, the container holding a desiccant, the upper portion having an input port and an output port, the lower portion having an input port and an output port, the output port of the upper portion fluidly connected to a first port of the container and the input port of the lower portion fluidly connected to a second port of the container; and,
(b) at least one clamp located on the upper and lower portions engageable with a fixture located on a device to securely affix the dryer to the device.

16. The dryer as set forth in claim 15 wherein the container includes a cartridge removably mounted between the upper and lower portions, the cartridge including:
(a) a tubular element with opposite ends closed by a top element and a bottom element;
(b) a first port located on the top element and a second port located on the bottom element, the first port and the second port fluidly connected, the desiccant located within the tubular element such that a carrier gas passes through the desiccant as the gas moves from the second port to the first port, the first port located on the top of the container such that when the container is positioned between the upper and lower portions, the first port of the container aligns with the input port of the upper portion and the second port of the container aligns with the output port of the lower portion;
(c) sealing means circumferentially located around the first port and the second port of the container such that when the container is clamped between the upper portion and the lower portion, the input port of the upper portion and the first port of the cartridge are sealed from the atmosphere and the output port of the lower portion and the second port of the container are sealed from the atmosphere.

17. A quick connect/disconnect apparatus comprising:
(a) a holder having a first portion and a second portion, the first and second portions rigidly connected and spaced apart so as to receive a cartridge therebetween, the first portion having an input port and an output port, the second portion having an input port and an output port, the output port of the first portion fluidly connectable to a first port of the cartridge and the input port of the second portion fluidly connectable to a second port of the cartridge;
(b) the first portion of the holder having a clamping mechanism operable after the cartridge has been placed in the holder to clamp the cartridge between the first portion and the second portion such that the output port of the first portion is in alignment with the first port of the cartridge and the input port of the second portion is in alignment with the second port of the container; and,
(c) at least one clamp located on the holder engageable with a fixture located on a device to securely affix the holder to the device.

18. The apparatus as set forth in claim 17, wherein said at least one clamp is located on the first portion further including a second clamp located on the second portion; and
wherein said fixture includes a first nipple and a second nipple, both the first and second nipples extending from the device, the first nipple having a collar, the collar located close to the device, the first nipple dimensioned to fit snugly within the input port of the first portion, the second nipple dimensioned to fit snugly within the output port of the second portion and the clamp engageable with said collar to secure said holder to said device.

19. The apparatus of claim 18, wherein the input port of the first portion and the output port of the second portion further include sealing means located within the input port of the first portion and the output port of the second portion so as to effect an air tight seal with said first and second nipples when said nipples are positioned within said input port of the first portion and said output port of the second portion.

20. A method of generating peroxy vapor including:
connecting a source of liquid peroxy solution with an interface for a vaporizer; clamping the unsaturated desiccant dryer cartridge in a flow path leading to the vaporizer; when the clamped desiccant dryer cartridge becomes partially or fully saturated, unclamping the particularly or fully saturated desiccant dryer cartridge from the flow path; and replacing the partially or fully saturated desiccant dryer cartridge with an unsaturated cartridge by clamping the unsaturated desiccant dryer cartridge in the flow path vaporizing the liquid peroxy solution to generate a peroxy vapor and entraining the peroxy vapor in dry air;

supplying the entrained peroxy vapor and air to a point of use;

returning air and water vapor from the point of use to a replaceable desiccant dryer;

moving the returned air and water vapor through the desiccant dryer;

discharging dry air from the desiccant dryer;

conveying the dry air to the vaporizer for entraining the peroxy vapor;

releasing the desiccant dryer when or before the desiccant dryer becomes saturated, and replacing the removed desiccant dryer with an unsaturated replacement desiccant dryer.

21. The method as set forth claim 20 wherein the source of peroxy liquid includes a canister containing a preselected volume of peroxy liquid and wherein clamping the unsaturated desiccant dryer cartridge includes:

clamping an unsaturated desiccant dryer cartridge which is loaded with an amount of desiccant which is sufficient to absorb the preselected volume.

22. The method as set forth in claim 20 further including:
connecting the removed desiccant dryer with a regenerator;
regenerating the removed desiccant dryer with the regenerator;
connecting the regenerated desiccant dryer with the vaporizer.

23. The method as set forth in claim 20, further including:
prior to clamping an unsaturated desiccant cartridge into the flow path, peeling off removable seals from end apertures of the desiccant dryer cartridge.

24. The method as set forth in claim 20, wherein releasing the desiccant dryer includes releasing clamps which allow nipples from being retracted from bores in end elements of the desiccant dryer and further including:

receiving nipples of a regeneration oven in the bores of the end elements;

regenerating the desiccant dryer;

detaching the bores of the desiccant dryer from the regeneration oven; and, mounting the bores of the desiccant dryer on the nipples associated with the vaporizer.

* * * * *